US012618820B2

(12) United States Patent
Bartolucci et al.

(10) Patent No.: US 12,618,820 B2
(45) Date of Patent: May 5, 2026

(54) CONTAINER FOR DETERMINING THE QUANTITY OF $CO_2$ ABSORBED AND/OR EXPELLED BY A SAMPLE OF MATTER OVER TIME

(71) Applicant: LESAFFRE ET COMPAGNIE, Paris (FR)

(72) Inventors: Jean-Charles Bartolucci, Hellemmes-Lille (FR); Florence Kapral, Comines (FR)

(73) Assignee: LESAFFRE ET COMPAGNIE, Paris (FR)

( * ) Notice: Subject to any disclaimer, the term of this patent is extended or adjusted under 35 U.S.C. 154(b) by 343 days.

(21) Appl. No.: 18/568,917

(22) PCT Filed: Jun. 13, 2022

(86) PCT No.: PCT/FR2022/051128
§ 371 (c)(1),
(2) Date: Dec. 11, 2023

(87) PCT Pub. No.: WO2022/263761
PCT Pub. Date: Dec. 22, 2022

(65) Prior Publication Data

US 2024/0280554 A1 Aug. 22, 2024

(30) Foreign Application Priority Data

Jun. 15, 2021 (FR) ....................................... 2106288

(51) Int. Cl.
*G01N 33/10* (2006.01)

(52) U.S. Cl.
CPC .................................... *G01N 33/10* (2013.01)

(58) Field of Classification Search
CPC ...................................................... G01N 33/00
See application file for complete search history.

(56) References Cited

U.S. PATENT DOCUMENTS 2,038,044 A 4/1936 Heald

FOREIGN PATENT DOCUMENTS

| | | | | |
|---|---|---|---|---|
| FR | 2528175 A1 * | 12/1983 | ............. | G01N 11/00 |
| FR | 3097965 A1 * | 1/2021 | ............... | G01N 1/24 |
| GB | 495849 A * | 11/1938 | ............... | G01N 7/22 |

OTHER PUBLICATIONS

International Search Report issued on Oct. 14, 2022, in corresponding PCT Patent Application No. PCT/FR2022/051128, 5 pages.

* cited by examiner

*Primary Examiner* — Jamel E Williams
(74) *Attorney, Agent, or Firm* — Maier & Maier, PLLC

(57) ABSTRACT

A container for determining the quantity of $CO_2$ absorbed and/or expelled by a sample of matter over time, including: a bottom compartment designed to receive a sample of matter, a top compartment receiving element for trapping $CO_2$, positioned in line with and communicating with the bottom compartment, and having an exhaust opening enabling gas to escape from the top compartment after it passes through the receiving element for trapping $CO_2$, a separation element, disposed between the bottom compartment and the top compartment, configured to enable gas to pass from the bottom compartment to the top compartment.

17 Claims, 10 Drawing Sheets

CONTAINER FOR DETERMINING THE QUANTITY OF $CO_2$ ABSORBED AND/OR EXPELLED BY A SAMPLE OF MATTER OVER TIME

FIELD

The present invention relates to a container for determining over time the quantity of carbon dioxide ($CO_2$) absorbed and/or expelled by a sample of matter, and in particular organic matter containing a leavening agent, such as for example yeast and/or leaven and/or leavening powder, such as for example dough containing bakery yeast.

The invention also relates to an appliance for determining over time the quantity of $CO_2$ absorbed and/or expelled by a sample of matter comprising such a container.

The invention also relates to a method for determining over time the quantity of $CO_2$ absorbed and/or expelled by a sample of matter.

BACKGROUND

The main functionality of a leavening agent, such as for example yeast and/or leaven and/or leavening powder, is to make dough rise. To do this, it produces $CO_2$ that quickly saturates the liquid phase of the doughy matrix and goes into vapour phase in numerous nuclei present in the dough at the end of kneading, thus producing expansion thereof, and will in the end product give rise to the numerous alveoli of the crumb. This expansion is possible only through the ability of the dough, in particular based on wheat flour, to retain gas.

The expansion of the dough can easily be observed. By placing a given mass of dough in a test piece and regularly measuring the height of the dough in the test piece, it is possible overall to evaluate this expansion, on the macroscopic level. This measurement is not very precise and, because of its macroscopic character, incorporates other phenomena such as the rheology of the dough. For example, for the same volume of dough, it is possible to have different dough heights ("flat" or "round" rising) and pockets of gas may possibly become housed between the dough and the test piece, which can falsify the measurements.

For a long time, appliances have existed that make it possible to measure the overall production of $CO_2$ by the yeast in the dough. The principle thereof is as follows: a piece of dough of known mass is placed in a hermetic pot; then, when the yeast produces $CO_2$, this causes an overpressure in the pot, firstly because the volume of dough increases, thus compressing the gas ceiling in the pot, and secondly because $CO_2$ is expelled by the dough in the gas ceiling of the pot, thus increasing the number of molecules of $CO_2$ present therein. This overpressure can be quantified by the displacement of a liquid, which corresponds to a direct measurement of volume, and/or by the use of a pressure sensor, as in some known measuring appliances, such as for example the measuring appliance marketed under the name Risograph® or Rhéofermentomètre®. The main advantage of these appliances is giving a kinetic vision of the phenomenon of production of $CO_2$ by a dough over time.

However, measuring the total production of $CO_2$ by a dough does not distinguish the part retained by the dough (giving rise to the expansion of the dough) from the part lost in the atmosphere. It therefore perfectly gives information about the fermentary activity of the yeast, but not on the proportion of $CO_2$ retained in the dough. However, many factors related both to the bread-making recipe (beginning with the quality of the flour) and to the process (e.g.: the frozen uncooked material), greatly modulate this retention/expulsion of the gas. Having a precise view on the kinetics of the gas retention/expulsion, apart from the rheological aspects, is therefore essential for being able to be in a position to uncouple the effects related to the fermentary activity of the yeast from the properties of the dough matrix.

The Rhéofermentomètre® mentioned above attempted to offer a solution to this problem. Such a solution consists in simultaneously measuring the pressure variation in the gas ceiling of the pot containing the dough via a direct channel, to obtain the total production of $CO_2$ by the dough, and via a channel passing through a $CO_2$ trap, comprising for example soda lime, and thus measure only the overpressure due solely to the expansion of the dough (de facto causing compression of the gas ceiling of the pot). In such an appliance, the $CO_2$ trap is connected to the pot containing the dough via a conduit, and is therefore separated from said pot and therefore from the gas ceiling of the pot containing the sample of dough.

The curves shown on the graph in FIG. 1A show an estimation of the change over time in the rate of release of $CO_2$ from a sample of dough in this type of device.

This solution is nevertheless not very satisfactory for taking account of the change over time of the retention/expulsion of $CO_2$ by a dough. This is because, and in accordance with the findings of the inventor, and as can be seen on the curves of the graph in FIG. 1B: if the flour-based dough is replaced by a reference system containing yeast but incapable of retaining $CO_2$, such as for example a beaker containing water, sugar and yeast, the curve representing the retention of $CO_2$ by said reference system, obtained by the pressure measurements via the channel with $CO_2$ trap, which should stagnate around a zero value (since the water does not swell when the sugar is transformed into $CO_2$ by the yeast), can in reality be substantially superimposed on the curve representing the increase in the total pressure in the pot obtained by the pressure measurements via the direct channel, in particular over short times. Everything happens is if the system (the beaker containing yeasted sugar solution) retained the $CO_2$ for more than an hour, which is not true. This appliance therefore does not fulfil the task of giving full information on the appearance of leakages of $CO_2$ in a dough, at least in an absolute manner, and cannot therefore be used for precisely meeting the objective of monitoring the kinetics of retention/expulsion of $CO_2$ in a dough, and more generally in a sample of matter, and in particular organic matter containing yeast, during the fermentation time.

A method that makes it possible to measure the rheological quality of fermented dough and to predict the behaviour of this dough during the thermal shock of baking is also known from the document FR2528175, published in 1983. The method also makes it possible to evaluate the behaviour of the dough during the gaseous rising, as well as the effects of the additives and improver before baking.

The device for implementing the method comprises:

- a thermostatically controlled vessel intended to contain the dough as well as a heavy mass and means for measuring the movement and recording the movement of the mass in abutment on the dough during its rising,
- means for measuring and recording at the same time the rate of release of gas formed during the fermentation of the dough and released from the dough, as well as the speed of the gas with carbon dioxide removed.

These measuring means include a nozzle on the lid of the vessel that is connected by a conduit to the inlet of a four-way control valve, controlled by a motor. One of the outlet ways of the control valve is connected by a first conduit to a pressure sensor that controls the recorder. Another way is connected to the sensor, by a conduit on which a $CO_2$ trap comprising an absorption mud containing potash is interposed. When the control valve rotates, the conduit of the nozzle is successively connected to the conduit in direct connection to the pressure sensor, then to atmosphere, then to the conduit indirectly connected to the pressure sensor by the $CO_2$ trap, then once again in direct connection with the sensor, and so on.

Such a device makes it possible to distinguish the moment when the proteins of the dough can no longer withstand the stresses due to the fermentation and the dough sinks, releasing $CO_2$, namely when two curves separate, a first curve representing the change in the pressure when the control valve is directly connected to the pressure sensor, the second curve representing the change in pressure when the control valve is connected to the pressure sensor, but only by the $CO_2$ trap, the ratio of the ordinates then indicating the proportion of $CO_2$ repelled (expelled) by the dough.

FR2528175 is based, like the Rhéofermentomètre®, on a $CO_2$ trap located at a distance from the enclosure containing the dough, and on the hypothesis that the gas that is released from the dough has been absorbed by the $CO_2$ trap, which is in reality not very reliable as disclosed on the curves in FIG. 1B produced by the inventors.

There is moreover another technical approach via the use of one or more $CO_2$ sensors in the atmosphere (consisting for example of one or more infrared probes) making it possible to deduce the kinetics of retention/expulsion of $CO_2$ from a sample of matter, and in particular dough containing a leavening agent, such as for example yeast and/or leaven and/or leavening powder. Use thereof is technically complex, since it is necessary to dynamically compensate for the change in the volume of the gas ceiling in the pot containing the dough because of the expansion of the sample of matter. Comparing in parallel the total production of $CO_2$ in the pot is tricky, since the two items of information are of very different natures (measurement of pressure for determining the total production of $CO_2$ by the dough in the pot and measurement of the concentration of $CO_2$ in the gas ceiling of variable volume for determining the quantity of $CO_2$ retained/expelled by the dough in the pot). Some known appliances use such technology, such as for example the appliance sold under the name Bluesens®.

There is also from the document GB 495 849, published in 1938, an appliance for measuring the change in the quantity of gas released in a fermentation, in particular a dough fermentation, the appliance including two gastight containers, one of the containers making it possible to measure all the gas produced by a first fraction of dough, and the other container measuring the gas that is formed during the fermentation but which remains retained by the dough. Each container is completely gastight and comprises a fixed bottom part and a top part in the form of a bell. The bell slides vertically sealingly with respect to the bottom part of the container, according to the change in internal pressure. The seal between the fixed part and the moving part of the container is obtained by immersing the container in a bath of oil circulated by a pump and heat-regulated. The change in the internal pressure at each container is measured indirectly, mechanically, by a pulley and counterweight system.

SUMMARY

The objective of the invention is therefore to overcome the drawbacks of the prior art for determining over time the quantity of $CO_2$ retained/expelled by a sample of matter, and in particular organic matter containing a leavening agent, such as for example yeast and/or leaven and/or leavening powder, making it possible to determine more reliably and more simply over time the quantity of $CO_2$ retained/expelled by a sample of matter, and in particular organic matter containing a leavening agent, such as for example yeast and/or leaven and/or also leavening powder.

Another aim of the present invention is to make it possible to determine over time the quantity of $CO_2$ retained/expelled by a sample of matter, and in particular organic matter containing a leavening agent, such as for example yeast and/or leaven and/or leavening powder, at reduced cost.

An appliance is proposed for determining the quantity of $CO_2$ absorbed by a sample of organic matter containing yeast and/or leaven and/or leavening powder, in particular dough, over time, comprising:

- a pressure-measuring means, and
- at least one container comprising:
  - a bottom compartment designed to receive a sample of matter,
  - a top compartment receiving means for trapping $CO_2$, positioned in line with and communicating with the bottom compartment, and having an exhaust opening enabling gas to escape from the top compartment after it passes through said means for trapping $CO_2$,
  - a separation means, disposed between the bottom compartment and the top compartment, configured to enable gas to pass from the bottom compartment to the top compartment,
- wherein the pressure-measuring means is connected to the exhaust opening of the top compartment of the container so as to be able to determine the change over time in the pressure in the bottom compartment receiving the sample of matter, after the gases coming from the bottom compartment pass into the top compartment of the container.

According to optional features of the invention, taken separately or in combination:

- the bottom compartment is at least partially, preferably entirely, made from a transparent material, for example from glass or from thermoplastic material, so as to enable an observer to view the content of the bottom compartment, and in particular to monitor the rising of the dough during fermentation,
- the bottom compartment, the top compartment and the separation means form a self-supporting assembly;
- the separation means includes a sieve in which a plurality of openings are formed configured so as to enable gas to pass from the bottom compartment to the top compartment;
- the means for trapping $CO_2$ include granules of soda lime;
- the granules of soda lime are disposed directly on the sieve, the openings of the sieve being configured so as to prevent the granules of soda lime passing from the top compartment to the bottom compartment;
- the container includes a top opening and the top compartment includes a bottom opening, the top opening of the container being aligned with the bottom opening of the top compartment, and wherein the separation means is also aligned with the top opening of the container and with the bottom opening of the top compartment;
- the top compartment is positioned entirely in the container, a plug, in particular removable, being positioned in the top opening of the container, so as to make said container gastight;

- the plug includes a through piercing positioned in line with the exhaust opening of the top compartment, so as to enable the gas from the top compartment to escape therefrom via said exhaust opening;
- the separation means is disposed at the bottom opening of the top compartment;
- the separation means is secured, and in particular removably, to the top compartment, optionally by means of securing means;
- the bottom compartment and the top compartment are secured removably;
- the container includes a peripheral wall substantially cylindrical in shape, and the top compartment also includes a peripheral wall substantially cylindrical in shape, with its axis coincident with the axis of the peripheral wall of the container;
- the container furthermore comprises a connection means, in particular removable, configured to enable the top compartment to be connected to a conduit, and in particular a flexible conduit, said connection means being positioned at the exhaust opening of the top compartment, extending through said exhaust opening;
- the connection means is held in position with respect to the top compartment by said exhaust opening of the top compartment, said connection means extending through the through piercing of the plug and being held in position with respect to the plug by the said through piercing;
- the top compartment includes a top wall, the exhaust opening being provided in said top wall.

The invention also relates to a method for determining overtime the quantity of $CO_2$ absorbed by a sample of matter, comprising organic matter containing yeast and/or leaven and/or leavening powder, in particular dough, comprising:

- /a/ provision of an appliance according to one of the embodiments of the invention;
- /b/ placing the sample of matter in the bottom compartment of the container,
- /c/ measuring the change in the pressure over time in the bottom compartment receiving the sample of matter, after the gases coming from the bottom compartment pass into the top compartment of the container.

When such a method is implemented, the pressure variation is due to the fermentation generating $CO_2$, which is retained by the sample (namely the absorbed $CO_2$), and not to the $CO_2$ expelled by the sample since the $CO_2$ expelled is eliminated by the means for trapping the $CO_2$ in the top compartment.

Since the fermentation reaction generates only $CO_2$ gas, it is possible to determine by calculation a quantity of $CO_2$ absorbed through knowledge of the internal volume of the container, or even to which there is added the internal volume of the flexible conduit connecting the exhaust opening to the pressure-measuring means.

The present disclosure also relates to a method for determining over time the quantity of $CO_2$ expelled by a sample of organic matter containing yeast and/or leaven and/or leavening powder, in particular dough, in the course of a fermentation reaction generating $CO_2$, comprising simultaneously a first measurement and a second measurement on a first fraction of sample and a second fraction of sample, with the same volume, and wherein said first measurement is configured to measure the change in pressure due solely to the quantity of gas absorbed, and the second measurement is configured to measure the change in pressure due to the quantity of gas absorbed and to the quantity of gas expelled and wherein the first measurement comprises:

- /a1/ providing an appliance according to one of claims 1 to 15 comprising the means for trapping the $CO_2$ received in the top compartment of the container;
- /b1/ placing the first fraction of sample of matter (M) in the bottom compartment of the container,
- /c1/ measuring the change in the pressure over time in the bottom compartment receiving the first fraction of the sample of matter, after the gases coming from the bottom compartment pass into the top compartment of the container, the $CO_2$ expelled by the sample eliminated by the means for trapping the $CO_2$, and wherein the second measurement comprises:
- /a2/ providing a second appliance according to one of claims 1 to 15 with no means for trapping the $CO_2$ received in the top compartment (3) of the container;
- /b2/ placing the second fraction of sample of matter in the bottom compartment of the container,
- /c2/ measuring the change in the pressure over time in the bottom compartment receiving the second fraction of the sample of matter, after the gases coming from the bottom compartment pass into the top compartment (3) of the container, with no means for trapping the $CO_2$,
- and wherein the quantity of $CO_2$ expelled by the sample is obtained from the difference between the second measurement and the first measurement.

BRIEF DESCRIPTION OF THE DRAWINGS

Other features, details and advantages of the invention will appear upon reading the detailed description hereinafter, and analysing the accompanying drawings, in which.

DETAILED DESCRIPTION

Figure 1A:
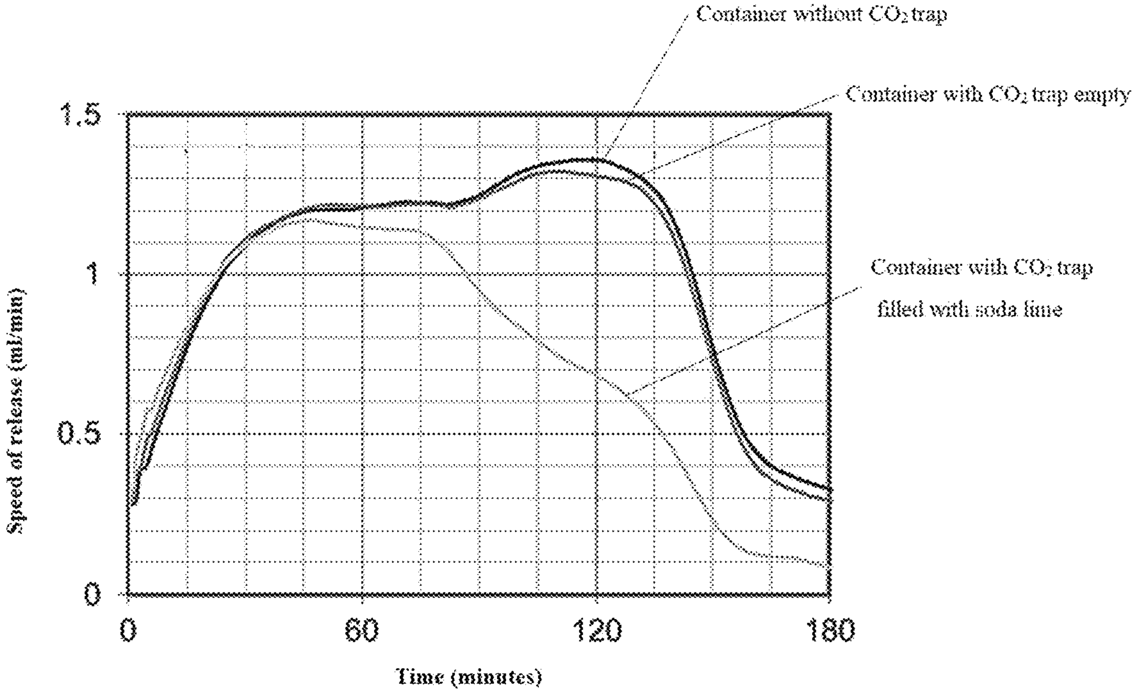
FIG. 1A shows a graph showing the change over time in the speed of release of $CO_2$ by a sample of dough established with an appliance of the prior art.

The drawings and the description hereinafter contain, essentially, elements of a definite nature. Therefore they may not only serve to gain a better understanding of the present disclosure, but also contribute to the definition thereof, where applicable.

In the whole of the present application, top/bottom and lateral, with regard to the position of certain elements of the container, mean in the normal position of use of the container according to the invention, with the top compartment positioned above the bottom compartment in a substantially vertical direction in space.

The invention relates to a container 1 for determining the quantity of $CO_2$ absorbed and/or expelled by a sample of matter M comprising:

- a bottom compartment 2 designed to receive a sample of matter M, and in particular organic matter containing a leavening agent, such as for example yeast and/or leaven and/or leavening powder, in particular dough (i.e. a mixture of flour, water, salt, yeast, etc),
- a top compartment 3 receiving means C for trapping $CO_2$, positioned in line with and communicating with the bottom compartment 2, and having an exhaust opening 31 enabling gas to escape from the top compartment 3 after it passes through said means C for trapping $CO_2$,
- a separation means 4, disposed between the bottom compartment 2 and the top compartment 3, configured to enable gas to pass from the bottom compartment 2 to the top compartment 3.

Such a container 1 advantageously makes it possible to position the means C for trapping $CO_2$ as close as possible to the sample of matter M. Thus all the $CO_2$ expelled by the sample of matter M over time is trapped by the means C for trapping $CO_2$.

Figure 2A:
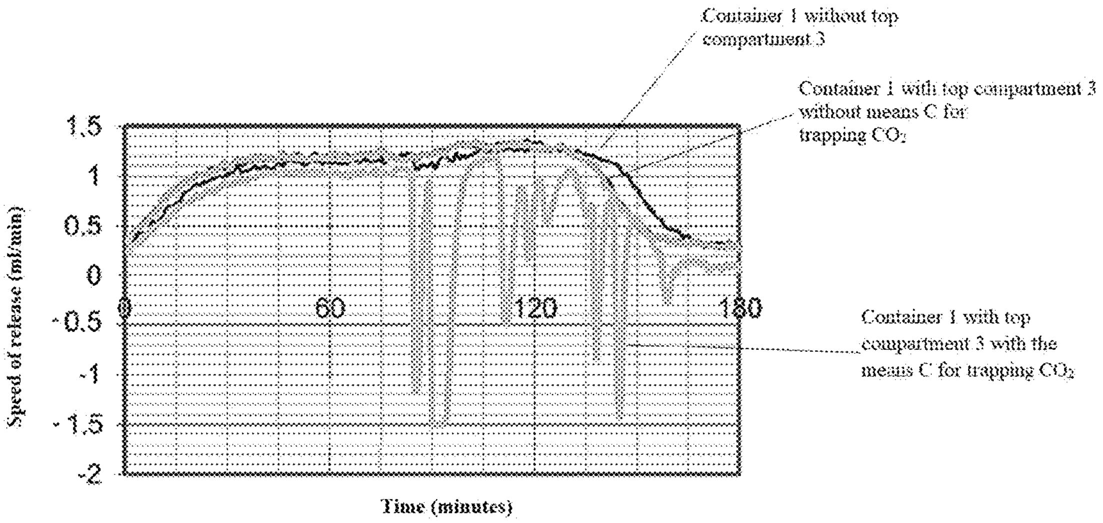
FIG. 2A shows a graph showing the change over time in the speed of release of $CO_2$ by a sample of dough established with an appliance according to the invention.

Because of this, by making for example a pressure measurement at the outlet of the top compartment 3, downstream of the exhaust opening 31, the measured pressure therefore reflects only the capacity for retention/expulsion of $CO_2$ by the sample of matter M, and variation thereof advantageously reflects the kinetics of retention/expulsion of $CO_2$ by the sample of matter M, and as can be seen more clearly on the curves of the graphs in FIGS. 2A (on dough), 2B and 2C (on liquid water+yeast+sugar system).

Figure 1B:
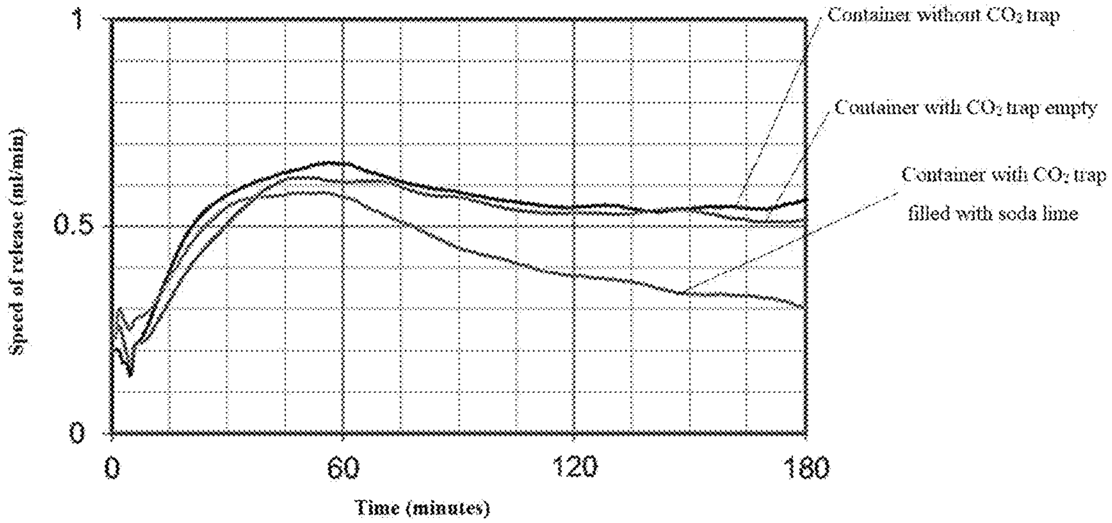
FIG. 1B shows a graph showing the change over time in the speed of release of $CO_2$ by a sample of water+yeast+sugar established with an appliance of the prior art.
Figure 2B:
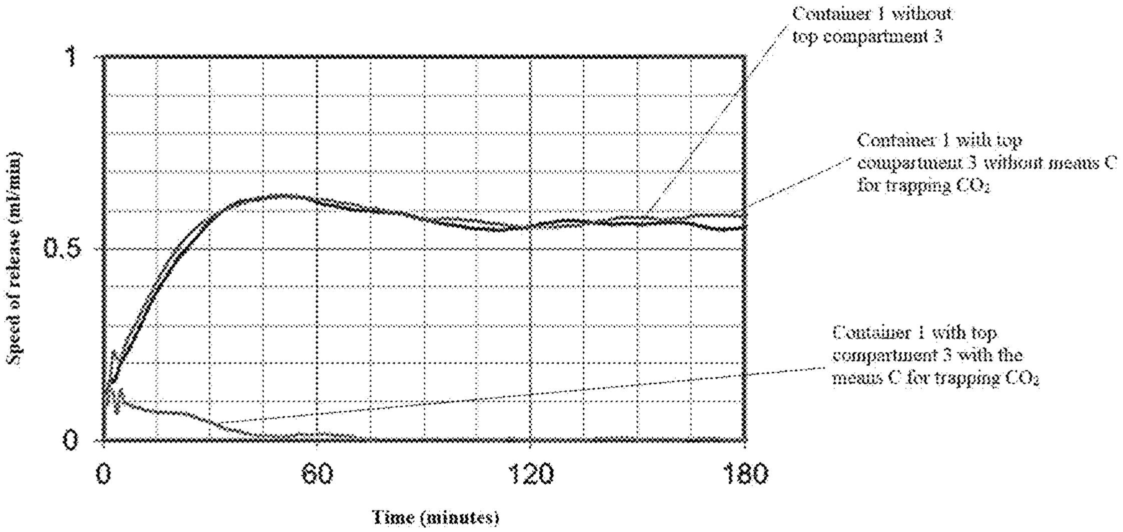
FIG. 2B shows a graph showing the change over time in the speed of release of $CO_2$ by a sample of water+yeast+sugar established with an appliance according to the invention.
Figure 2C:
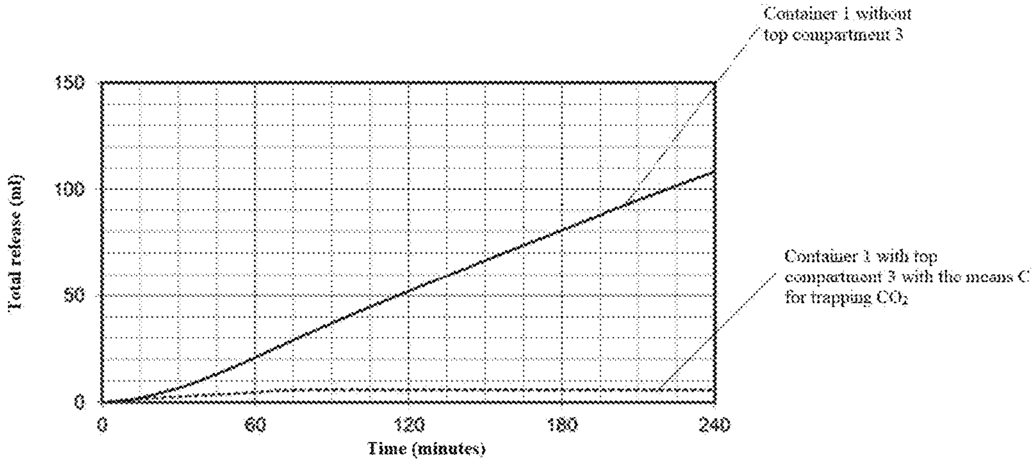
FIG. 2C shows a graph showing the change over time in the total quantity of $CO_2$ released by a sample of water+yeast+sugar established with an appliance according to the invention.

Moreover, and in accordance with the findings of the inventor, if a sample of a reference system containing yeast but incapable of retaining $CO_2$, as described above, is placed in the bottom compartment 2 of the container 1, such as for example a beaker containing water, sugar and yeast, the curve representing the retention of $CO_2$ by said reference system, obtained by the pressure measurements via the exhaust opening 31 of the top compartment 3 of the container 1, stagnates around a substantially zero value, as can be seen on the curves of the graphs in FIGS. 2B and 2C, which is in accordance with what occurs in said bottom compartment 2, since water does not retain $CO_2$, and contrary to the measurements made with an appliance and a container of the prior art, as explained above, and as can be seen on the curves of the graph in FIG. 1B.

Thus all the $CO_2$ expelled by a sample of matter M, and in particular dough, disposed in the bottom compartment 2, is therefore trapped by the means C for trapping $CO_2$, disposed in the top compartment 3.

The container 1 according to the invention therefore proves to be particularly advantageous for determining the change over time in the quantity of $CO_2$ retained/expelled by a sample of matter M, and in particular organic matter containing a leavening agent, such as for example yeast and/or leaven and/or leavening powder, in particular dough, reliably, and as can be seen for example on the curves of the graphs in FIGS. 2A to 2C.

Figure 2D:
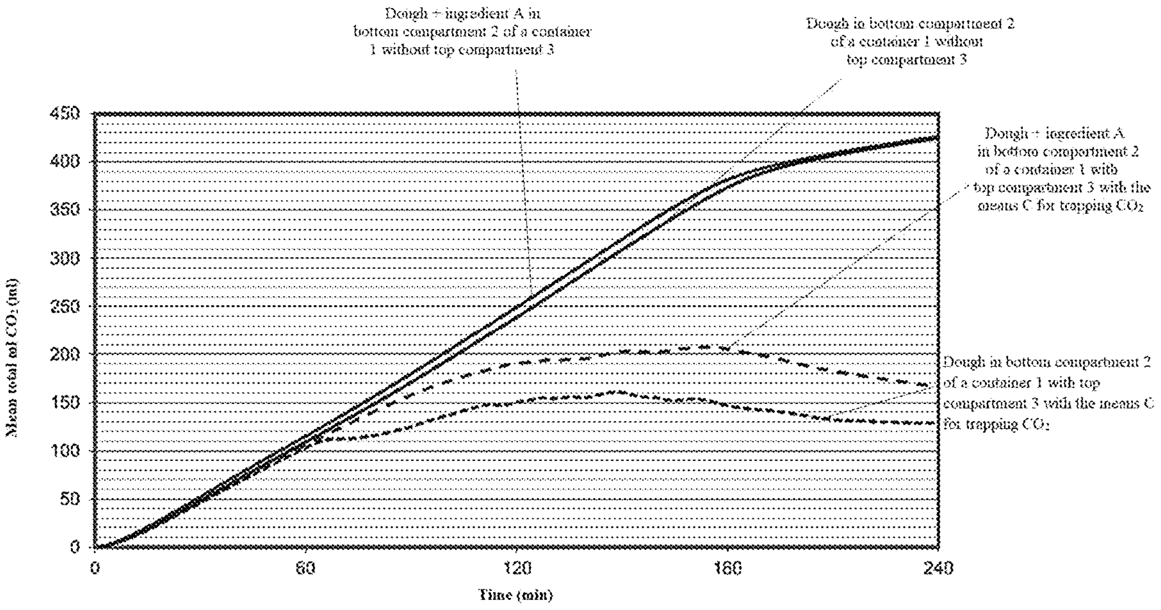
FIG. 2D shows a graph showing the change over time in the total quantity of $CO_2$ released by a sample of dough with or without an ingredient A.

Thus it becomes possible to particularly reliably determine the influence of various parameters on the change over time in the quantity of $CO_2$ retained/expelled by a sample of matter M, and in particular organic matter containing a leavening agent, such as for example yeast and/or leaven and/or leavening powder, in particular dough. In particular, as can be seen on the graph in FIG. 2D, the inventors were able to determine, by means of the container 1 according to the invention, that adding an ingredient A in a dough composition had no influence on the total production of $CO_2$ by the dough (the two curves in solid lines are substantially superimposed), but had an influence on the quantity of $CO_2$ retained/expelled by said dough over time (the sample of dough containing ingredient A retains more $CO_2$ over time than a sample of dough that has none, as shown by the two curves in broken lines). This would not have been possible with the techniques and appliances of the prior art.

In addition, such a container 1 has a particularly simple design that enables it to have a reduced cost.

The bottom compartment 2 can advantageously be produced, at least partially, preferably entirely, from a transparent material, for example glass or thermoplastic material, so as to enable an observer to view the content of the bottom compartment 2.

The top compartment 3 can advantageously be produced, at least partially, preferably entirely, from a rigid material, such as for example a plastics material or a metal material, and in particular aluminium.

According to one embodiment, the bottom compartment 2, the top compartment 3 and the separation means 4 form a self-supporting assembly.

This advantageous arrangement facilitates the handling, use and manufacture of the container 1 according to the invention.

Figure 7A:
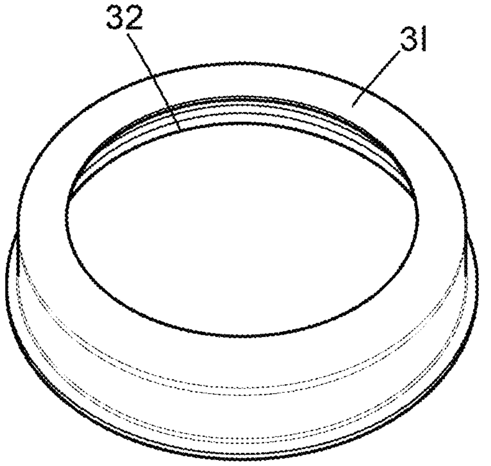
FIG. 7A shows a perspective view of the bottom part of the top compartment of a container according to one embodiment of the invention.
Figure 7B:
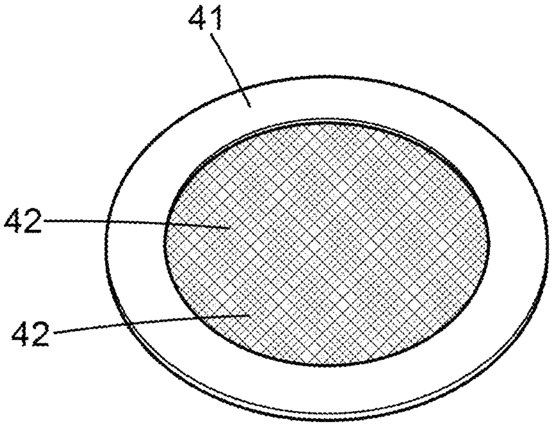
FIG. 7B shows a perspective view of the sieve of a container according to one embodiment of the invention.
Figure 8:
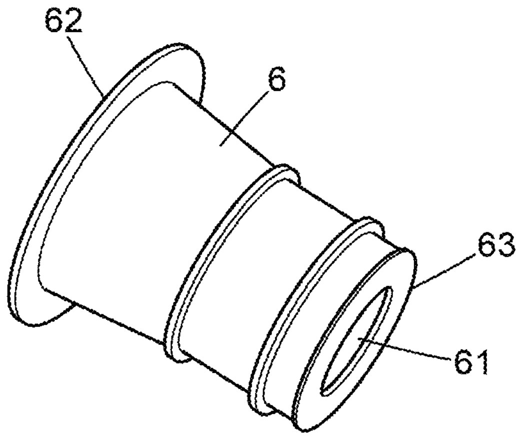
FIG. 8 shows a perspective view of the connection means of a container according to one embodiment of the invention.
Figure 9A:
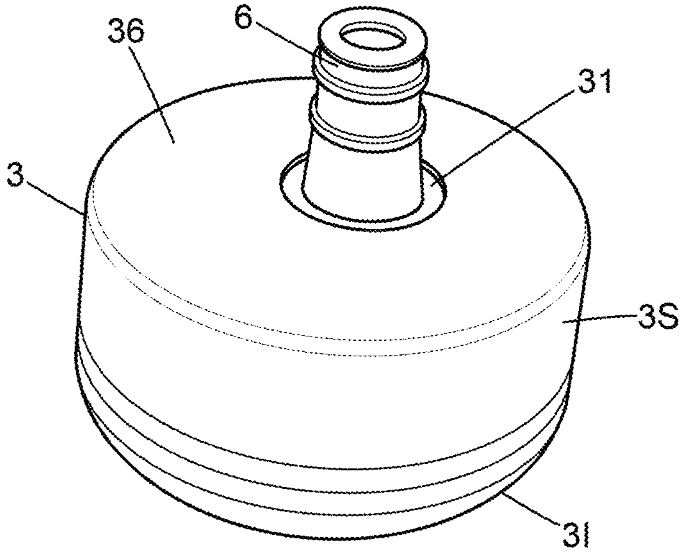
FIG. 9A shows a perspective view of the top compartment of a container according to one embodiment of the invention.
Figure 9B:
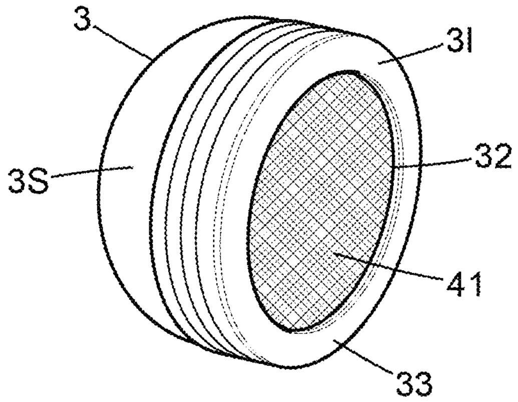
FIG. 9B shows a perspective view of the top compartment of a container according to one embodiment of the invention.

According to one embodiment, and as can be seen more particularly on FIGS. 7B and 9B, the separation means 4 includes a sieve 41 in which a plurality of openings 42 are provided, configured so as to enable gas to pass from the bottom compartment 3 to the top compartment 2.

The separation means 4 thus has a simple design and reduced cost.

The sieve 41 can for example be produced from metal, and in particular from stainless steel.

Advantageously, the openings 42 can have a width of between 150 μm and 350 μm, preferably between 200 μm and 300 μm.

In order to facilitate access to said means C for trapping $CO_2$, as well as optionally to said separation means 4, the top compartment 3 can advantageously be produced in two removable parts: a top part 3S and a bottom part 31. A thread can advantageously be provided on the periphery of the top part 3S and on the periphery of the bottom part 31, so as to be able to assemble/disassemble the bottom part 31 and the top part 3S of the top compartment 3 by screwing/unscrewing.

Figure 3:
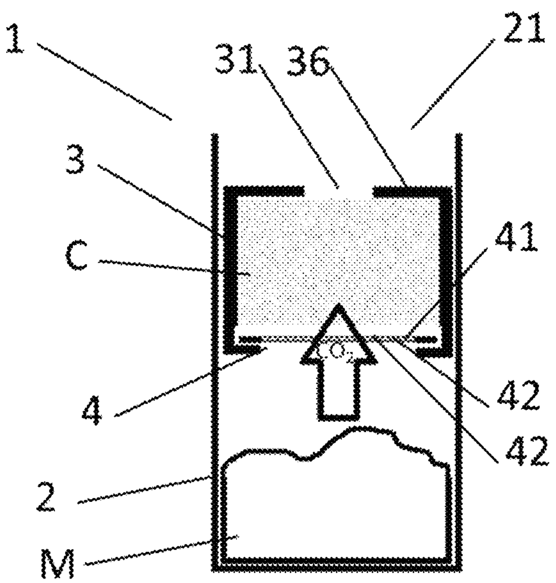
FIG. 3 shows a schematic view of a container according to one embodiment of the invention.
Figure 4:
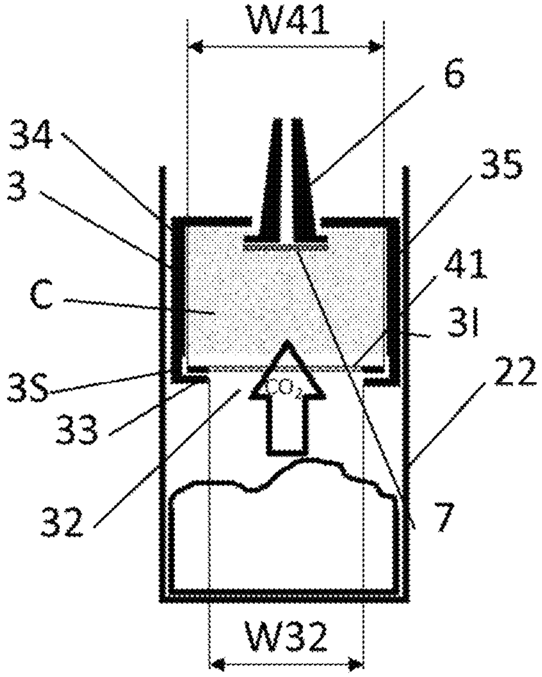
FIG. 4 shows a schematic view of a container according to one embodiment of the invention.
Figure 5:
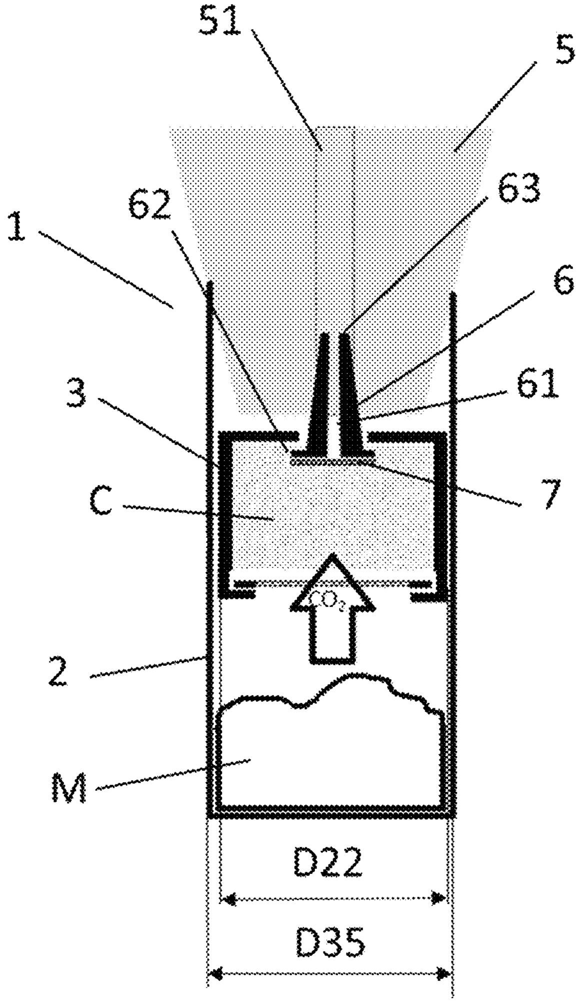
FIG. 5 shows a schematic view of a container according to one embodiment of the invention.
Figure 6:
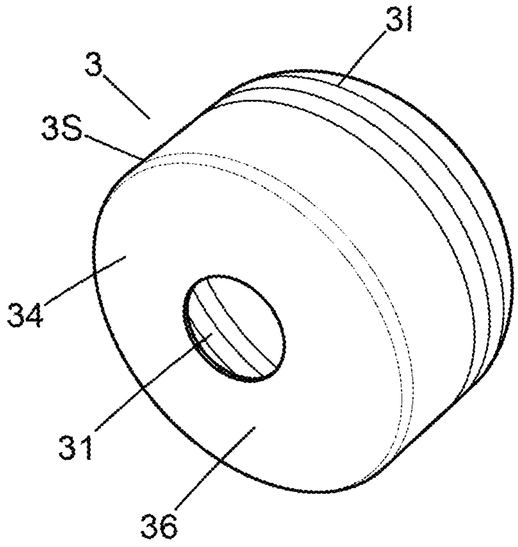
FIG. 6 shows a perspective view of the top compartment of a container according to one embodiment of the invention.

According to one embodiment, and as can be seen more particularly on FIGS. 3 to 5, the means C for trapping $CO_2$ include granules C of soda lime.

The granules of soda lime are well known elements that make it possible to trap $CO_2$. The main components of soda lime are generally calcium hydroxide: $Ca(OH)_2$ and sodium hydroxide: NaOH.

The granules of soda lime are particularly effective for trapping $CO_2$, in that they react therewith so as to form water, in accordance with the following chemical reactions:

$$H_2O + CO_2 = H^+ + HCO_3$$

$$NaOH + H_2CO_3 = NaHCO_3 + H_2O$$

$$2NaHCO_3 + Ca(OH)_{2+} = 2NaOH + CaCO_3 + H_2O$$

The use of granules of soda lime as means C for trapping $CO_2$ also has the advantage that, as soon as they are no longer able to react with the $CO_2$ to trap it, it simply suffices to replace them with new granules of soda lime for the container 1 according to the invention to become operational again.

The quantity of granules of soda lime C is adjusted according to the quantity of $CO_2$ to be trapped and the volume available in the top compartment 3 of the container 1.

According to one embodiment, and as can be seen more particularly on FIGS. 3 to 5, the granules C of soda lime are disposed directly on the sieve 41, the openings 42 in the sieve 41 being configured so as to prevent the granules C of soda lime passing from the top compartment 3 to the bottom compartment 2.

This advantageously makes it possible to simplify the design of the container 1 according to the invention, in that it is not necessary to provide an additional means for ensuring the holding of the granules C of soda lime in the top compartment 3.

According to one embodiment, and as can be seen more particularly on FIGS. 3 to 5, 7A and 9B, the container includes a top opening 21 and the top compartment 3 includes a bottom opening 32.

The top opening 21 of the container can advantageously be aligned with the bottom opening 32 of the top compartment 3.

Advantageously, the separation means 4, and in particular the sieve 41, can also be aligned with the top opening 21 of the container 1 and with the bottom opening 32 of the top compartment 3.

Thus the container 1 can have a reduced footprint and ensure optimum passage of the $CO_2$ from the bottom compartment 2 to the top compartment 3 through the separation means 4.

According to one embodiment, the top compartment 3 is positioned entirely in the container 1. Advantageously, and as can be seen more particularly on FIG. 5, a plug 5, in particular removable, can be positioned in the top opening 21 of the container, so as to make said bottom compartment 2 airtight.

By virtue of this advantageous arrangement of the invention, the airtightness of the container is ensured, so that all the $CO_2$ expelled by the sample of matter M over time necessarily passes through the top compartment 3, and therefore through the means C for trapping $CO_2$.

Alternatively, and without departing from the scope of the present invention, the airtightness of the bottom compartment 2 could be provided by the top compartment 3. In particular, the top compartment 3 can be configured so as to close off the top opening of the bottom compartment 2 when at least partly received therein. Equally, a sealing means secured to the top compartment 3 can be provided, and in particular a gasket positioned on the periphery of the peripheral wall 35 of the top compartment 3.

Advantageously, the plug 5 can be produced from elastomer material.

According to one embodiment, the plug 5 includes a through piercing 51 positioned in line with the exhaust opening 31 of the top compartment 3, so as to enable the gas from the top compartment 3 to escape therefrom via said exhaust opening 31.

According to one embodiment, the separation means 4, and in particular the sieve 41, is disposed at the bottom opening 32 of the top compartment 3.

This advantageously makes it possible to position the means C for trapping $CO_2$ as close as possible to the bottom compartment 2, and therefore to the sample of matter M.

According to one embodiment, the separation means 4, and in particular the sieve 41, is designed to be secured, and in particular removably, to the top compartment 3, optionally by means of securing means.

In particular, when said separation means 4, and in particular the sieve 41, is secured removably to the top compartment 3, this facilitates removal thereof, for example for carrying out maintenance thereof.

According to one embodiment, and as can be seen more particularly on FIGS. 4 and 9B, the top compartment 3 includes a bottom wall 33 wherein the bottom opening 32 is provided.

Advantageously, the sieve 41 can have a width W41 greater than the width W32 of the bottom opening 32, so as to rest in abutment on the bottom wall 33 of the top compartment 3.

Thus the sieve 41 can advantageously be held in position in the top compartment 3 while being "sandwiched" between said bottom wall 33 and the granules C of soda lime.

Equally, in order to reinforce the holding in position of the sieve 41 in the top compartment, a removable elastic ring can also be provided, with a width substantially equal to the width W41 of the sieve 41, designed to bear on the sieve 41 while remaining immobile with respect to the bottom wall 33 of the top compartment 3, so as to keep it in abutment against the bottom wall 33 of the top compartment 3 with the sieve 41 interposed between the elastic ring and the bottom wall 33.

According to one embodiment, the top compartment 3 includes a removable cover 34, designed to allow access to the interior of the top compartment 3 when removed.

Said cover 34 can in particular form the top part 31 of the top compartment 3, as described above.

The removable cover 34 thus facilitates access to the interior of the top compartment 3, and in particular to the means C for trapping $CO_2$, in particular for carrying out maintenance thereof, for example to change the granules C of soda lime.

According to one embodiment, the bottom compartment 2 and the top compartment 3 are designed to be secured removably.

This advantageous arrangement of the invention facilitates maintenance of the container 1 according to the invention, and facilitates access to the interior of the bottom compartment 2, and in particular to be able to position therein or remove the sample of material M. This simplifies the design of the container 1 according to the invention in that it is not necessary to provide an additional access opening to the interior of the bottom compartment 2.

According to one embodiment, the container 1 includes a substantially cylindrically shaped peripheral wall 22, and the top compartment 3 also includes a substantially cylindrically shaped peripheral wall 35, with its axis coincident with the axis of the peripheral wall 22 of the bottom compartment 2.

The plug 5 can advantageously have substantially a frustoconical shape, so as to provide the airtightness of the container by following the shape of the peripheral wall 22 of the container.

According to one embodiment, the container 1 furthermore comprises a connection means 6, in particular removable, configured to allow a connection of the top compartment 3 to a conduit, and in particular a flexible conduit, said connection means 6 being positioned at the exhaust opening 31 of the top compartment 3, extending through said exhaust opening 31.

As can be seen on FIGS. 4, 5, 8 and 9A, the connection means 6 can for example have a substantially frustoconical shape, so as to facilitate the connection and holding of a conduit, and in particular a flexible conduit. One or more annular ribs can be provided on the periphery of the connection means 6, so as to facilitate the holding in position of a conduit, and in particular a flexible conduit, thereon.

The connection means 6 can thus have a through piercing 61 extending between a bottom longitudinal end 62 and a top longitudinal end 63. The bottom longitudinal end 62 can advantageously be positioned inside the top compartment 3, while the top longitudinal end 63 can be positioned outside the top compartment 3.

A filtration means 7, such as for example a porous film, in particular made from nylon, can be secured at the bottom longitudinal end 62, so as to filter the gases passing through said through piercing 61 and thus prevent dust passing through said through piercing 61, which would risk for example damaging a pressure measuring means, positioned downstream.

Such a connection means 6 has a simple design and reduced cost. It can in particular be a case of a standard commercially available connection means.

According to one embodiment, the connection means 6 is held in position with respect to the top compartment 3 by said exhaust opening 31 of the top compartment 3, said connection means 6 extending through the through piercing 51 of the plug 5, in particular with its through piercing 61 in line with the through piercing 51 of the plug 5, and being held in position with respect to the plug 5 by said through piercing 51.

By virtue of this advantageous arrangement of the invention, the connection 6 can also fulfil a function of holding in position the top compartment 3 with respect to the bottom compartment 2, by providing a transmission of force between the top compartment 3 and the plug 5, which is held in position with respect to the bottom compartment 2.

Alternatively, or in addition, in order to ensure the holding in position of the top compartment 3 with respect to the container, the diameter D35 of the peripheral wall 35 of the top compartment 3 can be substantially equal to the diameter D22 of the peripheral wall 22 of the container, to within any fitting clearance, and so that the peripheral wall 22 is, at least partially, rubbing against the peripheral wall 35 of the top compartment 3.

According to one embodiment, the top compartment 3 includes a top wall 36, the exhaust opening 31 being provided in said top wall 36.

Advantageously, the top wall 36 can be formed in the top part 3S of the top compartment 3 and/or in the cover 34.

Figure 10:
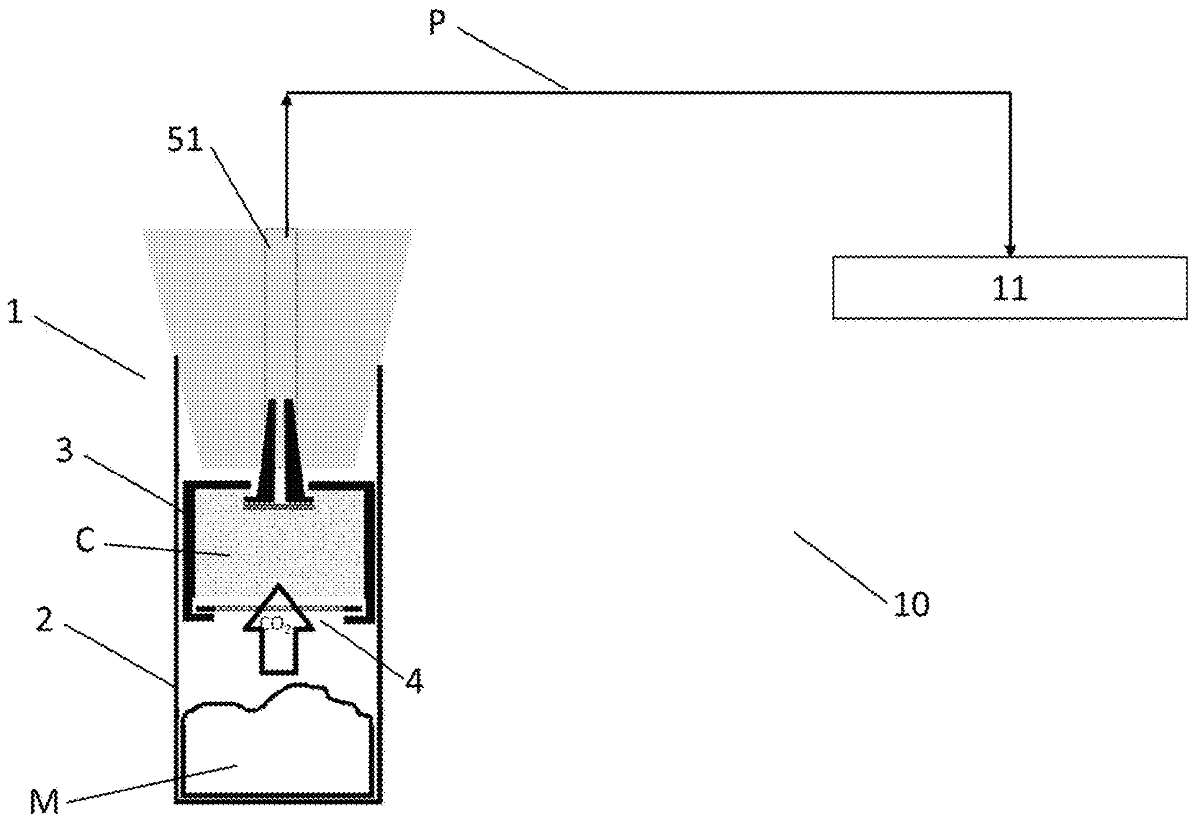
FIG. 10 shows a perspective view of an appliance according to one embodiment of the invention.

The invention also relates, as can be seen on FIG. 10, to an appliance 10 for determining over time in the quantity of $CO_2$ absorbed and/or expelled by a sample of matter M, and in particular organic matter containing a leavening agent, such as for example yeast and/or leaven and/or leavening powder, in particular dough, comprising:

- a means 11 for measuring the pressure,
- at least one container 1 according to one of the embodiments of the invention described above.

Advantageously, the pressure-measuring means 11 can be designed to be connected to the exhaust opening 31 of the top compartment 3 of the container 1 so as to be able to determine the change over time in the pressure in the bottom compartment 2 receiving the sample of matter M, after the gases coming from the bottom compartment 2 pass into the top compartment 3 of the container 1.

Such an appliance 10 advantageously makes it possible to know simply and reliably the change in the pressure in the bottom compartment 2 of the container 1 due to the capacity for expulsion/retention of $CO_2$ by said sample of matter M, and in particular in order to know the change over time in the quantity of $CO_2$ retained and/or expelled over time by a sample of matter M, and in particular organic matter containing a leavening agent, such as for example yeast and/or leaven and/or leavening powder, in particular dough.

Advantageously, the appliance can be produced using a commercially available appliance, such as for example the appliance marketed under the name Risograph® described above, with only a few adaptations.

The appliance 10 can advantageously include a plurality of containers 1 according to the invention, so as to make simultaneous pressure measurements of various containers 1, and so as to simultaneously determine the change in the pressure over time in the bottom compartment 2 of these containers 1, and in particular in order to know the change over time in the quantity of $CO_2$ retained and/or expelled over time by a plurality of samples of matter M.

The pressure measuring means 11 can in particular be connected to the exhaust opening 31 of the top compartment 3 of the container 1, in particular via the plug 5 and/or the connection means 6, by means of a conduit P, and advantageously a flexible conduit.

The pressure measuring means 11 may for example be a pressure sensor connected to a control unit.

All the arrangements described previously relate to an appliance for determining over time the quantity of $CO_2$ absorbed and/or expelled by a sample of matter M applied to the appliance 10 according to the invention.

The invention also relates to a method for determining over time the quantity of $CO_2$ absorbed by a sample of matter M (namely retained by the sample), and in particular organic matter containing a leavening agent, such as for example yeast and/or leaven and/or leavening powder, in particular dough, comprising:

/a/ provision of a container according to one of the embodiments of the invention described above;

/b/ placing the sample of matter M in the bottom compartment 2 of the container 1, /c/ measuring the change in the pressure over time in the bottom compartment 2 receiving the sample of matter M, after the gases coming from the bottom compartment 2 pass into the top compartment 3 of the container 1.

Advantageously, the method according to the invention can be implemented in the appliance 10 according to an embodiment of the invention, as described above.

When such a method is implemented, the pressure variation is due to the fermentation generating $CO_2$ that is retained by the sample (namely the absorbed $CO_2$), and not to the $CO_2$ expelled by the sample since the $CO_2$ expelled is eliminated by the means for trapping the $CO_2$.

Since the fermentation reaction generates only $CO_2$ gas, it is possible to determine by calculation a quantity of $CO_2$ absorbed (retained by the sample) through knowledge of the internal volume of the container, or even to which there is added the internal volume of the flexible conduit connecting the exhaust opening to the pressure-measuring means.

Such a method advantageously makes it possible to know simply and reliably the change in the pressure in the bottom compartment 3 of the container 1 caused by the retention of $CO_2$ by the sample of matter M, and in particular in order to know the change over time in the quantity of $CO_2$ retained over time by a sample of matter M, and in particular organic matter containing a leavening agent, such as for example yeast and/or leaven and/or leavening powder, in particular dough, during the fermentation reaction.

The present description also relates to a method for determining over time the quantity of $CO_2$ expelled by a sample of organic matter containing yeast and/or leaven and/or leavening powder, in particular dough, during a fermentation reaction generating $CO_2$.

Such a method simultaneously comprises a first measurement on a first fraction of sample and a second measurement and a second fraction of sample. The first fraction and the second fraction have the same volume and are typically obtained on a sample, in particular a freshly prepared dough.

The first measurement is configured to measure the change in pressure due solely to the quantity of gas absorbed and therefore makes possible to determine the quantity of $CO_2$ absorbed (or retained), as previously explained, whereas the second measurement is configured to measure the change in pressure due not only to the quantity of gas absorbed but also to the quantity of gas expelled and therefore makes it possible to determine the total quantity of $CO_2$ generated by the fermentation (absorbed and expelled).

The quantity of $CO_2$ expelled is determined by difference between the second measurement and the first measurement.

In particular, the first measurement comprises:

/a1/ providing a first appliance according to the present description comprising the means C for trapping the $CO_2$ received in the top compartment of the container;

/b1/ placing the first fraction of sample of matter in the bottom compartment 2 of the container 1, /c1/ measuring the change in the pressure over time in the bottom compartment 2 receiving the sample of matter M, after the gases coming from the bottom compartment 2 pass into the top compartment 3 of the container 1, the $CO_2$ expelled by the sample eliminated by the means for trapping the $CO_2$.

The second measurement, made simultaneously with the first measurement, comprises:

/a2/ providing a second appliance according to the present description, but without means C for trapping the comprising the means C for trapping the $CO_2$ received in the top compartment 3 of the container 1;

/b2/ placing the second fraction of sample of matter M in the bottom compartment 2 of the container 1, /c2/ measuring the change in the pressure over time in the bottom compartment 2 receiving the second sample of matter M, after the gases coming from the bottom compartment 2 pass into the top compartment 3 of the container 1, without means for trapping the $CO_2$.

Such a method advantageously makes it possible to know the change over time in the quantity of $CO_2$ expelled over time by a sample of matter M, and in particular organic matter containing a leavening agent, such as for example yeast and/or leaven and/or leavening powder, in particular dough, during the fermentation reaction.

As can be seen on the curves on the graphs in FIGS. 2A and 2B, the method according to the invention makes it possible for example to know the change over time in the rate of expulsion/retention of $CO_2$ by a sample of matter M, and in particular a dough. The sawtooth curve in FIG. 2A shows in fact the change in the rate of expulsion of $CO_2$ of a sample of dough.

Equally, as explained above, the method according to the invention also makes it possible to particularly reliably determine the influence of various parameters on the change over time in the quantity of $CO_2$ retained/expelled by a sample of matter M, and in particular organic matter containing a leavening agent, such as for example yeast and/or leaven and/or leavening powder, in particular dough. In particular, as explained above and as can be seen on the graph in FIG. 2D, the inventors were able to determine that adding an ingredient A in a dough composition had no influence on the total production of $CO_2$ by the dough, but had an influence on the quantity of $CO_2$ retained/expelled by said dough overtime, which would not have been possible with the methods of the prior art.

All the provisions described previously related to determining over time the quantity of $CO_2$ absorbed and/or expelled by a sample of matter M received in the bottom compartment 2 of a container 1 according to one of the embodiments of the invention described above apply to the method according to the invention.

Naturally, other embodiments would have been able to be envisaged by a person skilled in the art without departing from the scope of the invention defined by the following claims.

The invention claimed is:

1. An appliance for determining the quantity of $CO_2$ absorbed by a sample of organic matter containing yeast and/or leaven and/or leavening powder, in particular dough, over time, comprising:

a pressure-measuring means, and at least one container comprising:

a bottom compartment designed to receive a sample of matter, a top compartment receiving means for trapping $CO_2$, positioned in line with and communicating with the bottom compartment, and having an exhaust opening enabling gas to escape from the top compartment after it passes through said means for trapping $CO_2$, a separation means, disposed between the bottom compartment and the top compartment, configured to enable gas to pass from the bottom compartment to the top compartment, wherein the pressure-measuring means is connected to the exhaust opening of the top compartment of the container so as to be able to determine the change over time in the pressure in the bottom compartment receiving the sample of matter after the gases coming from the bottom compartment pass into the top compartment of the container.

2. The appliance according to claim 1, wherein the bottom compartment is at least partially, preferably entirely, made from a transparent material, for example glass or thermoplastic material, so as to enable an observer to view the content of the bottom compartment.

3. The appliance according to claim 1, wherein the bottom compartment, the top compartment and the separation means form a self-supporting assembly.

4. The appliance according to claim 1, wherein the separation means includes a sieve in which a plurality of openings are provided, configured so as to enable gas to pass from the bottom compartment to the top compartment.

5. The appliance according to claim 1, wherein the means for trapping $CO_2$ include granules of soda lime.

6. The appliance according to claim 5, wherein:

the separation means includes a sieve in which a plurality of openings are provided, configured so as to enable gas to pass from the bottom compartment to the top compartment, and the granules of soda lime are disposed directly on the sieve, the openings in the sieve being configured so as to prevent the granules of soda lime passing from the top compartment to the bottom compartment.

7. The appliance according to claim 1, wherein the container includes a top opening and the top compartment includes a bottom opening, the top opening of the container being aligned with the bottom opening of the top compartment, and wherein the separation means is also aligned with the top opening of the container and with the bottom opening of the top compartment.

8. The appliance according to claim 7, wherein the top compartment is positioned entirely in the container, a plug, in particular removable, being positioned in the top opening of the container, so as to make said container airtight.

9. The appliance according to claim 8, wherein the plug includes a through piercing positioned in line with the exhaust opening of the top compartment, so as to enable the gas from the top compartment to escape therefrom via said exhaust opening.

10. The appliance according to claim 7, wherein the separation means is disposed at the bottom opening of the top compartment.

11. The appliance according to claim 1, wherein the bottom compartment and the top compartment are secured removably.

12. The appliance according to claim 1, wherein the container includes a substantially cylindrically shaped peripheral wall, and the top compartment also includes a substantially cylindrically shaped peripheral wall, with its axis coincident with the axis of the peripheral wall of the container.

13. The appliance according to claim 1, furthermore comprising a connection means, in particular removable, configured to allow connection of the top compartment to a conduit, and in particular a flexible conduit, said connection means being positioned at the exhaust opening of the top compartment, extending through said exhaust opening.

14. The appliance according to claim 13, wherein:

the plug includes a through piercing positioned in line with the exhaust opening of the top compartment, so as to enable the gas from the top compartment to escape therefrom via said exhaust opening, and the connection means is held in position with respect to the top compartment by said exhaust opening of the top compartment, said connection means extending through the through piercing of the plug and being held in position with respect to the plug by said through piercing.

15. The appliance according to claim 1, wherein the top compartment includes a top wall, the exhaust opening being provided in said top wall.

16. A method for determining over time the quantity of $CO_2$ absorbed by a sample of organic matter containing yeast and/or leaven and/or leavening powder, in particular dough, during a fermentation reaction generating $CO_2$, comprising:

/a/ providing an appliance according to claim 1 comprising the means for trapping the $CO_2$ received in the top compartment of the container;

/b/ placing the sample of matter in the bottom compartment of the container,

/c/ measuring the change in the pressure over time in the bottom compartment receiving the sample of matter, after the gases coming from the bottom compartment pass into the top compartment of the container, the $CO_2$ expelled by the sample eliminated by the means for trapping the $CO_2$.

17. A method for determining over time the quantity of $CO_2$ expelled by a sample of organic matter containing yeast and/or leaven and/or leavening powder, in particular dough, in the course of a fermentation reaction generating $CO_2$, comprising simultaneously a first measurement and a second measurement on a first fraction of sample and a second fraction of sample, with the same volume, and wherein said first measurement is configured to measure the change in pressure due solely to the quantity of gas absorbed, and the second measurement is configured to measure the change in pressure due to the quantity of gas absorbed and to the quantity of gas expelled, and wherein the first measurement comprises:

/a1/ providing a first appliance according to claim 1 comprising the means for trapping the $CO_2$ received in the top compartment of the container;

/b1/ placing the first fraction of sample of matter in the bottom compartment of the container, /c1/ measuring the change in the pressure over time in the bottom compartment receiving the sample of matter, after the gases coming from the bottom compartment pass into the top compartment of the container, the $CO_2$ expelled by the sample eliminated by the means for trapping the $CO_2$, and wherein the second measurement comprises:

/a2/ providing a second appliance according to claim 1 with no means for trapping the $CO_2$ received in the top compartment of the container, /b2/ placing the first fraction of sample of matter in the bottom compartment of the container, /c2/ measuring the change in the pressure over time in the bottom compartment receiving the second fraction of the sample of matter, after the gases coming from the bottom compartment pass into the top compartment of the container, with no means for trapping the $CO_2$, and wherein the quantity of $CO_2$ expelled by the sample is obtained from the difference between the second measurement and the first measurement.

* * * * *